(12) United States Patent
Dunham et al.

(10) Patent No.: US 8,092,790 B2
(45) Date of Patent: Jan. 10, 2012

(54) METHODS OF MAKING FORMULATIONS TO AFFECT INSECT BEHAVIOR AND/OR BIRD BEHAVIOR

(75) Inventors: Charles F. Dunham, Spokane, WA (US); C. Eugene Olsen, Spokane, WA (US); John Cochran, Newberry, FL (US); Deborah M. Cochran, legal representative, Newberry, FL (US)

(73) Assignee: Bug Buster, Ltd., Spokane, WA (US)

( * ) Notice: Subject to any disclaimer, the term of this patent is extended or adjusted under 35 U.S.C. 154(b) by 0 days.

(21) Appl. No.: 12/987,298

(22) Filed: Jan. 10, 2011

(65) Prior Publication Data
US 2011/0104099 A1    May 5, 2011

Related U.S. Application Data

(60) Division of application No. 11/238,675, filed on Sep. 29, 2005, now Pat. No. 7,867,479, which is a continuation-in-part of application No. 10/447,656, filed on May 28, 2003, now Pat. No. 6,958,146.

(60) Provisional application No. 60/614,956, filed on Sep. 29, 2004.

(51) Int. Cl.
*A01N 37/44* (2006.01)
*A01N 37/34* (2006.01)
*A01N 37/10* (2006.01)
*A01N 65/00* (2006.01)

(52) U.S. Cl. .......................................... 424/84; 514/535
(58) Field of Classification Search .................. None
See application file for complete search history.

(56) References Cited

U.S. PATENT DOCUMENTS 5,296,226 A * 3/1994 Askham ...................... 424/405
6,958,146 B2 * 10/2005 Askham et al. ............... 424/84

OTHER PUBLICATIONS

M. El ATQY. Food Chemical Changes.Food Science Technology[online], [retrieved on Jan. 29, 2011]. Retrieved from the Internet:< URL: http://www.azaquar.com/en/iaa/index.php?cible=ca_alteration.*

* cited by examiner

*Primary Examiner* — Janet L. Epps-Smith
*Assistant Examiner* — Courtney Brown
(74) *Attorney, Agent, or Firm* — Brian J. Pangrle

(57) ABSTRACT

Various exemplary compounds, compositions, methods and devices are disclosed. An exemplary composition or formulation includes methyl anthranilate, fatty acid and an amine such as, but not limited to, monoethanolamine or triethanolamine. Such an exemplary composition is optionally an emulsion. An exemplary method applies an exemplary compound to an insect nest. Such an exemplary compound may be in a composition or formulation. Exemplary compounds optionally include semiochemicals of insects, plants and/or animals. Other exemplary compounds, compositions, methods and devices are also disclosed.

15 Claims, 2 Drawing Sheets

Triethanolamine (TEA) emulsion
Storage ~ 1 year

Methyl anthranilate emulsion added to standard bird repellant emulsion
Storage ~ 1 year Triethanolamine (TEA) emulsion diluted to application strength
Mix date~ 2 months prior

METHODS OF MAKING FORMULATIONS TO AFFECT INSECT BEHAVIOR AND/OR BIRD BEHAVIOR

RELATED APPLICATIONS

This application is a divisional application of U.S. patent application having Ser. No. 11/238,675, filed on Sep. 29, 2005 (issued as U.S. Pat. No. 7,867,479), which is a continuation-in-part (CIP) of co-pending U.S. patent application having Ser. No. 10/447,656, filed on May 28, 2003, which are both incorporated herein by reference. The U.S. patent application having Ser. No. 11/238,675 claims the benefit of U.S. Provisional Application having Ser. No. 60/614,956, filed Sep. 29, 2004, which is incorporated herein by reference including the text, figures and appendix thereof.

TECHNICAL FIELD

The subject matter disclosed herein generally relates to compounds, compositions, methods, devices to manage insects or birds.

BACKGROUND

Insecticides are often used to manage insects in or on plants. Most insecticides require contacting an insect to work effectively. Where insects exist on an exposed surface of a plant, contact may be readily achieved via spraying or other delivering means. However, where insects exist at least partially in a plant (e.g., in a stem, in a leaf, in a fruit, in a seed, etc.), contacting often becomes more difficult or practically impossible. The plant, or relevant part thereof, can create a barrier that slows transport of an insecticide. Further, an insect residing at least partially in a plant, or relevant part thereof, may exist in a favorable environment where effectiveness of an insecticide is reduced. For example, if an insect resides in a seed, the seed may act as a barrier to transport and as a shelter from unfavorable environmental conditions. Under such circumstances, the insect may be exposed to the insecticide at a tolerable rate (e.g., where metabolism can break down the insecticide and thereby prevent accumulation of a fatal concentration of insecticide). Exposure at tolerable levels may lead to an increase in insect tolerance to the insecticide and hence a decrease in effectiveness of the insecticide. At worst, the insecticide can longer achieve acceptable insect kill rates. Therefore, a need exists for means to affect insect behavior in a manner that increases and/or maintains insecticide effectiveness. Various exemplary compounds, compositions, methods, devices, etc., described herein aim to meet this need and/or other needs. Other needs addressed herein include those that pertain to formulations, which are essentially compositions generally aimed as marketable products having characteristics that improve storage, delivery, effectiveness, etc.

DETAILED DESCRIPTION

Figure 1:
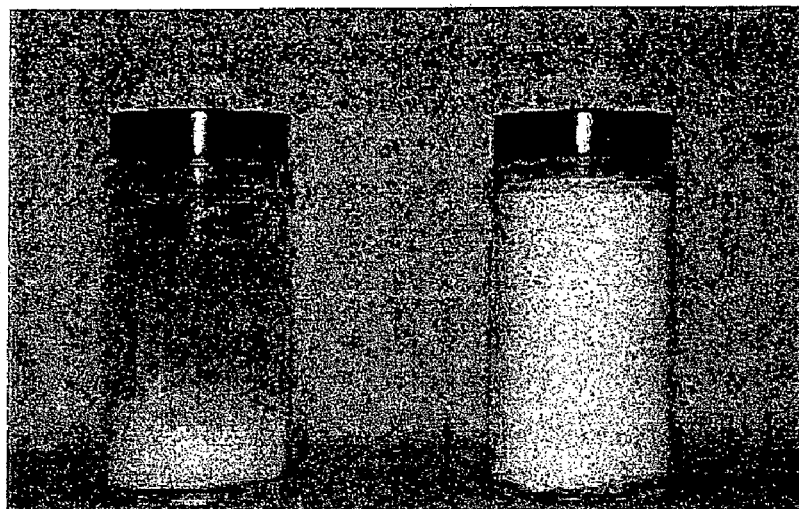
FIG. 1 is a photograph comparing a bird repellant with an emulsion using an alkali metal salt with an emulsion using an amine-based functional group.

The following description includes the best mode presently contemplated for practicing various described implementations. This description is not to be taken in a limiting sense, but rather is made merely for the purpose of describing the general principles of the various implementations. The scope of the described implementations should be ascertained with reference to the issued claims.

Overview

Exemplary compositions, formulations, methods, devices, etc., include one or more exemplary compounds that can affect insect behavior or bird behavior. Where insects are involved, such compounds generally act to stimulate insects wherein the term "stimulate" includes, but is not limited to, irritate, attract, alarm and/or repel. Hence, at times, such compounds may be 10 referred to as stimulants with stimulation subclasses such as attractant, repellant, irritant, etc. Of course, such compounds may affect other insect behavior. Further, such compounds may act as and/or be insect semiochemicals. Yet further, such compounds may act as bird repellents. As described herein, semiochemicals include, but are not limited to, pheromones, allomones, and kairomones. Such exemplary compositions, formulations, methods, devices, etc., optionally include adjuvant use (e.g., to modify or facilitates the action of another treatment).

An exemplary composition includes an insecticide and one or more exemplary compounds that can affect insect behavior. Another exemplary composition includes one or more exemplary compounds that can affect insect behavior and an insect mutagen, teratogen and/or other compound that can otherwise affect insect genetics. Various exemplary compositions include one or more exemplary compounds that can affect insect behavior and that can act as a bird repellent.

An exemplary method includes applying one or more exemplary compounds that can affect insect behavior to a plant and applying an insect toxin (e.g., insecticide, etc.) to the plant. Another exemplary method includes applying an exemplary composition to a plant, wherein the composition includes an insect toxin and one or more exemplary compounds that can affect insect behavior. Various exemplary methods apply an exemplary compound that can affect insect behavior and that can act as a bird repellent.

Exemplary Compounds for Affecting Insect Behavior

Exemplary compositions, formulation, devices, methods, etc., include one or more compounds that can affect insect behavior. Such compounds may 10 be stimulants that may irritate, attract, alarm and/or repel one or more insect species. Of course, such compounds may affect other insect behavior.

Further, such compounds may act as and/or be insect semiochemicals. Yet further, such compounds may act as bird repellents (i.e., affect bird behavior). Compounds that can affect insect behavior typically include saturated and unsaturated carbon-carbon bonds. Some exemplary compounds include cyclic carbon-carbon bonds. Some exemplary compounds include aromatic carbon-carbon bonds. Most exemplary compounds include at least one oxygen atom bound to at least one carbon atom. Such compounds may exist as aldehydes, alcohols, carboxylic acids, ketones, esters, ethers and/or other types of compounds. Of course, depending on pH, etc., deprotonation or protonation may occur or a compound may exist as a salt. With respect to salts, any suitable counter ion may suffice, such as, but not limited to, sodium ions, potassium ions, ammonium ions, monoethanolamine ions, diethanolamine ions, triethanolamine ions, and/or other nitrogen containing ions.

Further, exemplary compounds that exist as ions may be paired with other ionic chemical species. For example, an exemplary compound that includes an amine may serve as a counter ion to an anionic chemical species and/or to neutralize an acid.

Some exemplary compounds that can affect insect behavior (e.g., stimulate insects) exist as non-cyclic alcohols. For example, 3,7-dimethyl-2,6-octadien-I-ol (formula weight of approximately 154 and marketed as Geraniol 980™, IFF, New Jersey) includes saturated and unsaturated carbon-carbon bonds and may exist as an alcohol and 3,7-dimethyl-6-octen-1-ol (formula weight of approximately 156 and marketed as Citronellol 950™; IFF, New Jersey) includes saturated and unsaturated carbon-carbon bonds and may exist as an alcohol.

Some exemplary compounds include a six carbon aromatic ring (e.g., a benzene ring) having one or more moieties (e.g., group or chain) bound thereto. In general, such exemplary aromatic compounds include a moiety that includes at least one oxygen atom. For example, methyl anthranilate (formula weight of approximately 151 and also known as methyl 2-aminobenzoate and having isomers methyl 3-aminobenzoate, etc.) has an ester moiety and 4-pentenophenone (formula weight of approximately 160 and marketed as LAVONAX™, IFF, New Jersey) has a ketone moiety. Other exemplary compounds, such as, bisabolene (formula weight of approximately 204), include an unsaturated six carbon ring and do not include any oxygen atoms.

An example structure for the exemplary compound methyl anthranilate (e.g., methyl 2-aminobenzoate, $C_8H_9NO_2$, formula weight approx. 151) is shown below as structure 1:

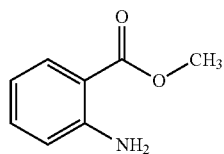

Methyl anthranilate, having an amine group, may act as a base, for example, capable of neutralizing acids.

An example structure for the exemplary compound 4-pentenophenone (e.g., 1-phenylpent-4-en-1-one, $C_{11}H_{12}O$, formula weight approx. 160) is shown below as structure 2:

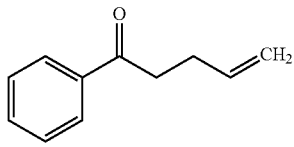

Based on the example structures 1 and 2, some exemplary compounds include a general structure given by structure 3:

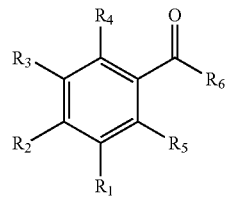

In the example structure 3, $R_1$, $R_2$, $R_3$, $R_4$, $R_5$ and $R_6$ are selected from a group that includes atoms H, N, C, and O. For example, in structure 1, $R_1$, $R_2$, $R_3$, and $R_4$ are H, $R_5$ is N (e.g., —$NH_2$) and $R_6$ is 0 (e.g., —$OCH_3$), while in structure 2, $R_1$-$R_5$ are H and $R_6$ is C (e.g., —$C_4H_7$). The example structure 3 has at least seven carbon atoms and at least one oxygen atom. In a simple form, the example structure 3 is benzaldehyde, which has a formula weight of approximately 106 (e.g., $R_1$-$R_6$ are H).

Some exemplary compounds include more than one cyclic carbon ring. For example, 2-naphthaldehyde, 1,2,3,4,5,6,7,8-octahydro-8,8-dimethyl (formula weight of approximately 196 and marketed as CYCLEMONE A™ and MELAFLEUR™, IFF, New Jersey) includes two adjoined cyclic carbon rings and an aldehyde moiety bound to one of the carbon rings and, the commercial product CYCLEMONE™, may include a ketone moiety bound to a carbon atom of one of the rings.

Some exemplary compounds include one or more nitrogen atoms. Such exemplary compounds may include an aromatic ring having a primary, 20 secondary, tertiary and/or quaternary amine nitrogen atom bound to a carbon atom of the aromatic ring. For example, aminobenzene (e.g., aniline, phenylamine, etc.) includes a primary amine nitrogen atom bound to an aromatic ring, the aforementioned exemplary compound methyl anthranilate includes an amine moiety bound to an aromatic ring and another exemplary compound includes a carbon bound to a nitrogen atom of a methyl anthranilate via a carbon-nitrogen double bond wherein the carbon atom is further bound to a carbon chain (e.g., an aldimine) that includes an aromatic six carbon ring.

Other exemplary compounds having a nitrogen moiety include, but are not limited to, anthranilic acid (formula weight of approximately 137 and also known as 2-aminobenzoic acid, etc.) and p- or o-aminoacetophenone or other variants thereof (formula weight of approximately 135), which includes a ketone moiety. Referring again to the example structure 3, anthranilic acid corresponds to an $R_x$, where x is a number from 1 to 5, of N (e.g., —$NH_2$) and $R_6$ of 0 (e.g., —OH as a protonated acid) and p-, o-, aminoacetophenone corresponds to an $R_x$, where x is a number from 1 to 5, of N (e.g., —$NH_2$) and $R_6$ of C (e.g., —$CH_3$).

Further, an exemplary compound may include a ring wherein the ring includes a nitrogen atom. For example, methyl nicotinate (formula weight of approximately 137 and a methyl ester of nicotinic acid) includes a nitrogen atom in a ring that also includes five carbon atoms. Exemplary compounds may include methyl-N methyl anthranilate (formula weight of approximately 165), which has a secondary amine nitrogen that does not form Schiff bases with aldehydes and hence has little or no tendency to form complexes with aldehydes, etc., which may discolor or reduce efficacy (e.g., due to "sugar-amine" browning, etc.).

Another exemplary compound is methyl salicylate ($C_8H_8O_3$, formula weight of approximately 151). With respect to example structure 3, $R_x$, where x is a number from 1 to 5, is 0 (e.g., —OH) and $R_6$ is 0 (e.g., —$OCH_3$).

Various aforementioned exemplary compounds have been shown to affect insect behavior while other exemplary compounds include structural similarities and/or moieties of such exemplary compounds. Various aforementioned exemplary compounds have been shown to act as insect semiochemicals while other exemplary compounds include structural similarities and/or moieties of such exemplary compounds. Exemplary compounds include semiochemicals or analogs thereof (e.g., natural or synthetic) that may be released by insects, plants, animals, etc. Further, an exemplary compound may affect different insects differently.

In particular, various aforementioned exemplary compounds that include a nitrogen atom have been shown to affect insect behavior. For example, methyl anthranilate and methyl nicotinate are insect semiochemicals released from the postpygidial gland of worker African army ants (e.g., Aenictinae *Aenictus* sp. nova, other *Aenictus*, etc.) and o-aminoacetophenone is an insect semiochemical released from queen honey bees (e.g., *Apis mellifera* L., other *Apis*, etc.) and apparently not from worker bees. During fights, queens often release rectal fluid with a strong smell of grapes, after which they temporarily stop fighting. The fluid, which includes o-aminoacetophenone, has an effect on behavior of worker bees. In small groups, the exemplary compound o-aminoacetophone repels bees and helps to terminate agonistic interactions between queen and worker bees. The exemplary compounds methyl anthranilate and o-aminoacetophone have also been shown to exhibit repellency to birds. In general, a semiochemical is a chemical produced by an animal, an insect and/or a plant, or a synthetic analog thereof, capable of affecting insect behavior. In some examples, a semiochemical is a chemical produced by an animal, an insect and/or a plant that plays a role in ecological interactions between an insect and animals, insects and/or plants.

Exemplary compounds include semiochemicals released by insects of the aculeate or order *Hymenoptera*(e.g., sawflies, parasitic wasps, wasps, ants, and bees). Exemplary compounds from the order *Hymenoptera* include those of the genus *Apis* and genus *Aenictus*. Exemplary compounds also include compounds released by insects of the order *Isoptera* (e.g., termites) whereas others include compounds released by insects of the orders *Homoptera*(Aphididae) and/or Thysanoptera. The order *Hymenoptera* includes the primary angiosperm pollinators (bees) and natural predators and parasitoids (ants, aculeate wasps, Parasitica) of other insects in many terrestrial biomes, and they have commensurate economic value in playing the same beneficial roles in crop pollination and in the control of harmful insects in agroecosystems. In general, bees can act as pollinators, not only of various crop plants, but of most of the known flowering plants.

Ants and wasps are important predators on insects, spiders and other arthropods and, less commonly, on small vertebrates. The larvae of both groups are largely, if not entirely, carnivorous. Since colony populations of some species of ants are often in excess of 50,000 larvae, it follows that considerable quantities of insect prey are collected by the foraging workers in order to feed these larvae. Hence, semiochemicals related to foraging and fighting can play an important role in survival. In particular, chemical communication via special alarm and/or attack semiochemicals can aid in insect defense and/or attack. For example, a semiochemical may deter predators and/or affect behavior of prey. Consider the exemplary compound methyl anthranilate, which deters birds and, as described in more detail below, affects behavior of insects that may be prey to *Hymenoptera* and/or *Isoptera*.

With respect to ants (e.g., Formicidae), Aenictinae includes true legionary or army ants belonging to the genus *Aenictus*. Legionary ants are known to be group raiders that do not have established nests and known to be specialized predators of other ant species. Further, colonies typically have a single queen and may number into the hundreds of thousands. The exemplary compounds methyl anthranilate and methyl nicotinate have been shown to be trail semiochemicals for *Aenictus*. Further, methyl anthranilate has been shown to trigger flight of sexuals from nest (e.g., *Camponotus* spp.).

With respect to bees, *Apis* includes honeybees (*Apis* spp., esp. *A. mellifera*). The exemplary compounds geraniol, nerol, neral, geranial, 1-heptanol, 2-phenyl-ethanol, nerolicacid, and geranolic acid have been shown to affect behavior of bees (e.g., *Panurgus banksianus, P. calacaratus*). Further, the exemplary compound 3,7-dimethyl-6-octen-1-ol (e.g., citronella') has been shown to affect behavior (e.g., act as a territory marker) of bees (e.g., *Apidae, Psithyrus*).

Exemplary compounds that are or act as semiochemicals typically have a formula weight from approximately 80 to approximately 300. In general, such exemplary compounds are volatile. Further, such exemplary compounds typically have from approximately 5 to approximately 20 carbons. Yet further, a relationship may exist between behavior and formula weight. For example, an alarm semiochemical may require quick dispersal to be effective and hence an alarm semiochemical may be quite volatile and/or have a formula weight that is less than other types of semiochemicals. In addition, an alarm semiochemical may be ephemeral to ensure duration proportionate to alarm stimulus.

Active space typically refers to a space within which an exemplary compound concentration is above a threshold level capable of affecting insect behavior, which is sometimes referred to as a response threshold level. Achieving at least a threshold level, maintaining at least a threshold level and/or reducing to below a threshold level may depend on volatility, evaporation, diffusion, etc., of an exemplary compound. Active space may be defined with respect to a ratio of molecules released per unit time to a response threshold level in terms of molecules per unit volume. This ratio may vary depending on target behavior. For example, a sex semiochemical may have a high ratio (e.g., due to a high release rate), an alarm semiochemical may have a lesser ratio and a trail semiochemical may have an even lesser ratio (e.g., due to a lower release rate). In general, release rate, duration of release and frequency of release determine semiochemical reserve and/or semiochemical production requirements.

Various aforementioned exemplary compounds may correspond to plant semiochemicals. For example, methyl anthranilate occurs in concord grapes and geraniol occurs in citrus plants, lemon grass, roses and palmarosa. Other plant semiochemicals include nerol, lavender absolute, jasmine absolute, and racemic borneol from *Dryobalanops aromatica* (e.g., optionally produced synthetically). Yet other plant semiochemicals include benzoin (also known as benzoylphenylcarbinol $C_{10}H_{12}O_2$, formula weight approximately 212), dimethyl benzyl carbinol ($C_{10}H_{14}O$, formula weight approximately 151), carbonyl acetate, d-limonene ($C_{10}H_{16}$, formula weight approximately 136) and dihydrolinalool ($C_{10}H_{20}O$, formula weight approximately 156).

Other exemplary compounds include dimethyl substituted oxy methyl cyclohexane, oxymethyl cyclohexane, propylidene phthalide, tridecene-2-nitrile, and methyl 2-pyrrolidone-5-carboxylate. For example, 2-undecyl acetate has been shown to be a mosquito attractant, ethyl ester of 2-methyl-3-pentenoic acid has been shown to be a house fly attractant and bisabolene has been shown to be a house fly repellent, alpha-terpineol has been shown to be a sand fly attractant and dimethyl substituted oxymethyl cyclohexene has been shown to be at least a black fly and mosquito attractant.

It has been shown that beneficial insects, such as *Deraeocoris brevis* (Uhler) and *Orius tristicolor* (White) may be attracted to (E)-3-hexenyl acetate on sticky cards. In addition it has been shown that *Geocoris pallens* Stal. and hover flies (Syrphidae) were attracted to methyl salicylate baited cards. *Stethorus penctum picipes* (Casey) was attracted to the exemplary compound methyl salicylate, which has also been demonstrated to attract green lacewing (*Chrysopa nigricornis* Bermeister). It has also been shown that *Thrips hawaiiensis, T. coloratus* and *Ceranisus menes* are attracted to the exemplary compound methyl anthranilate. Moreover it has been shown that the exemplary compound methyl anthranilate did not attract a closely related *T. tabaci* species. It has also been shown that methyl anthranilate is also attractive to *Thaumatomyia glabra* (Meigen) flies.

An exemplary compound may affect two different insect species differently. For example, such a compound may attract a beneficial species and repel a detrimental species. In another example, one or more of exemplary compounds may attract beneficial insects to a plant, animal structure or space to prey upon detrimental insects. In this example, the detrimental insects are controlled without the use of an insecticide. In another example, one or more exemplary compounds are used to repel beneficial insects to prevent mortality of the beneficial insects due to application of an insecticide. In such an example, an exemplary compound might be combined with an insecticide wherein the exemplary compound keeps the beneficial insects away from the insecticide that is being used to control certain pest species insects. Of course, such an exemplary compound may be applied prior to the insecticide to drive the beneficial insects out of the plants, animals, structures or spaces prior to the application of an insecticide where they may be harmed by its presence.

Exemplary Compositions

An exemplary composition includes one or more exemplary compounds that can affect insect behavior and an insecticide. Another exemplary composition includes one or more compounds that can affect insect behavior and an insect mutagen, teratogen and/or other compound that can affect insect genetics. Various exemplary compositions include one or more compounds that can affect insect behavior and that can act as a bird repellent.

An exemplary composition includes an exemplary compound and a pyrethrin and/or a pyrethroid insect toxin. For example, an exemplary composition includes an exemplary compound and lambda-cyhalothrin (marketed as WARRIOR®, Syngenta, Willmington, Del.). Over the years, semi-synthetic derivatives of the chrysanthemumic acids have been developed as insecticides and are referred to generally as pyrethroids. Pyrethroids tend to be more effective than natural pyrethrins while they are less toxic to mammals. A common synthetic pyrethroid is allethrin. As described herein, the term "pyrethrins" refers to the natural insecticides derived from, for example, chrysanthemum flowers; the term "pyrethroids" refers to synthetic chemical analogs thereof, and the term "pyrethrum" is a general name covering both pyrethrins and pyrethroids. In general, pyrethroids have formula weights in a range from approximately 316 to approximately 374, the range optionally due to differences in types and amounts of esters in a pyrethrum mixture.

Another exemplary composition includes an exemplary compound and esfenvalerate (marketed as ASANA®, E.I. du Pont de Nemours and Co., Delaware). Esfenvalerate, also known as (+)Alpha-cyano-3-phenoxybenzyl-(+)-alpha-(4-chlorophenyl)isovalerate, has a formula weight of approximately 420, includes three aromatic six carbon rings and has a water solubility of less than approximately 0.3 mg/L at approximately 25° C.

Insecticides that may be suitable for use in an exemplary composition include malathion (e.g., also known as S-1,2-bis (ethoxycarbonyl)ethyl 0,0-dimethylphosphorodithioate, $C_{10}H_{19}O_6PS_2$, formula weight approximately 330); dimethoate (e.g., also known as 0,0-dimethyl S-methylcarbamoylmethylphosphorodithioate, C5H12NO3PS2, formula weight approximately 229); 0,0-dimethyl 0-(2,4,5-trichlorophenyl)-phosphoro-thioate (C8H8CI3O3PS, formula weight approximately 322); zeta-cypermethrin (e.g., also known as S-cyano(3-phenoxyphenyl)methyl (+/−)-cis/trans-3-(2,2-dichloetheny1)-2,2-dimethylcyclopropanecarboxylate, formula weight approximately 416); and bifenthrin (e.g., also known as (2-methyl-1,1-biphenyl-3-y1)-methyl-3-(2-chloro-3,3,3-trifluoro-1-propenyl)-2,2-dimethyl cyclopropanecarboxylate, formula weight of approximately 423).

An exemplary composition includes an exemplary compound having a formula weight less than approximately 300 and an insecticide having a formula weight greater than approximately 300. Such formula weights may be specific and/or average formula weights. Another exemplary composition includes an exemplary compound having a formula weight less than approximately 220 and an insecticide having a formula weight of greater than approximately 220. Yet another exemplary composition includes an exemplary compound having less than three aromatic rings and an insecticide having three aromatic rings. In general, a smaller molecule can access locations more readily than a larger molecule. For example, a relatively hydrophobic exemplary compound (e.g., insoluble or slight water solubility, especially when not a salt) may more readily access locations (e.g., in or on a plant, in or on an insect, etc.) compared to a larger, relatively hydrophobic (e.g., insoluble or slight water solubility, especially when not a salt) insecticide. Some refer to slight water solubility as a range from 0.1 percent by weight to approximately 1 percent by weight.

An exemplary composition includes an exemplary compound and an insect toxin (e.g., insecticide, etc.) wherein the exemplary compound can affect insect behavior and can act as a bird repellent. For example, methyl anthranilate and o-aminoacetophone can affect insect behavior and can act as bird repellents. Further, an exemplary composition includes methyl anthranilate and/or o-aminoacetophone and a pyrethroid insect toxin. Of course, other combinations are possible wherein one or more exemplary compounds are selected and used to form a composition that includes a pyrethroid insect toxin.

An exemplary composition includes a commercially available product marketed as BIRDSHIELD™ (Bird Shield Repellent Corp., Spokane, Wash.) having methyl anthranilate as an active ingredient and includes an insect toxin. Information disclosed in U.S. Pat. No. 5,296,226, entitled "Bird Repellent Compositions", is incorporated by reference herein.

Compositions may include other compounds to achieve stability of one or more exemplary compounds and/or insecticides. Other compounds may participate in structuring compositions (e.g., lamellar, micelles, liquid crystalline, multilamellar vesicles, etc.) and/or facilitating dispensing, dispersion, time-release, etc.

Exemplary Methods

An exemplary method includes applying one or more exemplary compounds that can affect insect behavior to a plant and applying an insect toxin to the plant. Another exemplary method includes applying one or more exemplary compounds to an animal, a structure and/or a space to affect insect behavior therein or thereon and applying an insect toxin to the same animal, structure and/or space. Yet another exemplary method includes applying an exemplary composition to a plant, an animal, a structure and/or a space (or proximate to a plant, an animal, a structure and/or a space) wherein the composition includes one or more exemplary compounds that can affect insect behavior and an insect toxin. Various exemplary methods apply an exemplary compound that can affect insect behavior and that can act as a bird repellent.

An exemplary method aims to reduce insecticide usage by applying one or more exemplary compounds and/or an exemplary composition. In general, such a method aims to reduce organic and/or inorganic insecticides usage per application wherein each application aims to control detrimental insects and/or pests of forests, agricultural crops, and/or home or garden horticulture.

Another exemplary method aims to reduce a number of insecticide applications to achieve pest control by applying one or more exemplary 20 compounds and/or an exemplary composition. For example, such an exemplary method may aim to reduce the number of insecticide applications or treatments required during a growing season of a plant as well as in, on or around animals, structures and spaces. Another exemplary method may aim to reduce the amount of insecticide in an exemplary composition required to achieve mortality in targeted insect pest species. Yet another exemplary method may aim to reduce the detrimental effects on beneficial insects by applying an exemplary composition. Another exemplary method may aim to attract beneficial insects to plants, animals, structures and/or spaces through the use of the exemplary compounds in and of themselves to plants, animals, structures and/or spaces.

Yet another exemplary method aims to reduce a need for adhering and/or spreading agents, which are typically used with insecticides. For example, the commercially available product marketed as BIRDSHIELD™, which includes the exemplary compound methyl anthranilate, includes fatty acids and/or surfactants. Use of such a product can reduce a need for adhering and/or spreading agents, for example, in an exemplary compositions and/or an exemplary method.

Another exemplary method aims to cause insects to experience a change in environmental conditions by applying one or more exemplary compounds and/or an exemplary composition. For example, an exemplary compound may cause an insect to at least partially (e.g., including fully) exit a first environment and at least partially enter a second environment. In this example, the first environment may be in a plant (e.g., in a stem, in a leaf, in a fruit, in a seed, etc.) and the second environment may be on a plant (e.g., on a stem, on a leaf, on a fruit, on a seed, etc.). Such a change may cause an insect to become exposed to detrimental environmental conditions (e.g., sun, lower or higher temperature, humidity, wind, movement, etc.) and/or to become exposed to predators or be caused to come in contact with an insecticide or another exemplary compound. Further, such a change may be irreversible in that an insect may not or cannot return to the first environment. Where the first environment includes a readily accessible food source, the insect may become food deprived. Various reasons exist for insect avoidance of reentry, including, but not limited to, an unpleasant sensation (e.g., odor, taste, etc.) or mortality.

Yet another exemplary method aims to expose an insect to an insecticide by applying one or more exemplary compounds and/or an exemplary composition. For example, an exemplary compound may cause an insect to at least partially exit a first environment and to enter at least partially a second environment wherein the second environment includes an insecticide.

In some instances, an exemplary compound may access a first environment more readily than an insecticide. In such instances, the exemplary compound causes an insect to at least partially exit the first environment and thereby become exposed to an insecticide. In some situations, the first environment may be considered a sanctuary. Also consider applying an insecticide and an exemplary compound directly to an insect food source where an insect resides at least partially in substrata of the food source. Upon exposure to the exemplary compound, the insect may emerge from the substrata and contact the insecticide. Once in contact with the insecticide, effectiveness of the insecticide (e.g., mortality rate, etc.) may be increased. Moreover, the quantity or amount of the insecticide required to cause mortality may be reduced.

EXAMPLES

Grapes and Fruit Flies

An exemplary compound, methyl anthranilate, was combined with fatty acid and used to attract insects, in particular, fruit flies (*Drosophila* spp.). This exemplary compound will also repel at least some birds. The exemplary compound attracted fruit flies. An exemplary compound, methyl anthranilate, was combined with fatty acid and applied to a surface (e.g., a treated surface) of a sticky trap and used to attract and to trap insects, in particular, fruit flies (*Drosophilia* spp.). This exemplary compound will also repel at least some birds.

A trial compared insect attraction for an untreated surface of a sticky trap and with a treated surface of a sticky trap. In less than one minute, the treated surface was covered with insects while only a few insects covered the untreated surface. Further trials demonstrated that the entire surface did not need to be treated for the exemplary compound to attract insects to the sticky trap.

A trial noted that effectiveness of the exemplary compound methyl anthranilate may be diminished in a competitive environment. For example, grape crushing and/or fermenting may release competitive agents. Hence, an exemplary method includes applying an exemplary compound only during periods where crushing and/or fermenting do not occur or applying an increased concentration or amount of an exemplary compound during such periods.

Corn and Corn-Borers

An exemplary compound, methyl anthranilate, was combined with fatty acid and applied to crop fields (again, this formulation will also repel at least some birds), contemporaneously, an insecticide having a pyrethrin, lambda cyalothrin, as an active ingredient was applied to crop fields (e.g., WARRIOR™). Within a day of treatment, corn ear worm larvae (corn ear worm (*Heliothus zea*)) littered the ground. In a trial that did not apply the exemplary compound, methyl anthranilate, and fatty acid, but did apply the insecticide, pyrethrin, corn ears were still infested with a significant number of corn ear worm larvae.

In another trial, an insecticide that included a pyrethrin, lambda cyalothrin, was applied to crop fields (e.g., WARRIOR™). In this trial limited morbidity of corn ear worm larvae was observed. Later, an exemplary compound, methyl anthranilate, combined with a fatty acid, was applied to the same crop field. Within a day, corn ear worm larvae littered the ground. An exemplary composition included an exemplary compound, methyl anthranilate, fatty acid and an insecticide that included a pyrethrin, lambda cyalothrin, as an active ingredient (e.g., WARRIOR™). The exemplary composition was applied to crop fields. Within a day of application, corn ear larvae littered the ground.

Application at or Near Beginning of a Season

An exemplary composition included an exemplary compound and an insecticide. The exemplary composition was applied to corn crops at the beginning of a growing season. At the end of the growing season, a significant improvement in efficacy of an insect control program was observed. In particular, the results indicated that a single application of an exemplary compound and/or exemplary composition was sufficient to control a certain insect species or group of insect species (e.g., compared to multiple treatments required in absence of the exemplary compound). An exemplary method includes applying an exemplary compound and/or an exemplary composition to crops at or near the beginning of a growing season. Of course, other application times may be appropriate as well. In general, such a method can reduce the number of applications of an insecticide and still achieve a desirable result.

Sunflowers

An insecticide such as ASANA™ (active ingredient esfenvalerate) is suitable for use in controlling banded sunflower moth (*Cochylis hospes*). An exemplary composition that included an exemplary compound, methyl anthranilate (e.g., BIRDSHIELD™), was applied to sunflowers. After application of the exemplary composition, sunflower heads (e.g., seed containing portion of a sunflower plant) were observed for sunflower seed head larvae and no significant number of seed head larvae was observed. In contrast, sunflowers that had an application of insecticide only, exhibited a significant number of seed head larvae and other insects including mites.

An insecticide, ASANA™, was applied to sunflowers. Approximately two weeks later, an exemplary compound, methyl anthranilate (e.g., BIRDSHIELD™ at 0.006%) was applied to the same sunflowers. Within a minute of application, sunflower seed head larvae began to appear on the surface of the sunflowers. The larvae exhibited behavior that included wiggling and squirming. This behavior caused the larvae to fall off of the flower portions of the sunflowers. In addition, the exemplary compound affected behavior of other insects on the treated sunflowers. For example, insects such as mites and spiders were observed to appear from spaces between maturing seeds and to subsequently fall off the flower portion of the sunflowers.

Comparison to DEET

An exemplary composition was compared to N,N-Diethyl-m-toluamide (DEET). The exemplary composition included an exemplary compound, methyl anthranilate (e.g., BIRDSHIELD™ at 0.006% methyl anthranilate), and an insecticide, esfenvalerate (e.g., ASANA™). A 24% DEET solution is often used in a standard evaluation process by entomologists for evaluating seed weevil (*Smicronyx* spp.) infestations. In trials, the exemplary composition was observed to be as effective as the 24% DEET. No insects were observed in sunflowers seed heads sprayed with the exemplary composition or the 24% solution of (DEET).

Trials with an Exemplary Compound

Trials involved applying an exemplary compound to larvae in a laboratory growing medium. Trials demonstrated that the exemplary compound affected insect behavior.

An exemplary compound, methyl anthranilate (e.g., BIRDSHIELD™) was applied to insects that were first allowed to adapt to a laboratory environment. A control group of insects were not exposed to the exemplary compound. Observations indicated that those in the control group remained in their laboratory growing medium while those exposed to the exemplary compound emerged quickly from the laboratory growing medium and began wiggling about.

Colonies of house flies (*Drosophila melanogater*) were selected for subsequent placement in covered Petri dishes wherein each Petri dish was divided into three sections. One of the sections, a center section, was used as a control. An exemplary compound, methyl anthranilate (e.g., BIRDSHIELD™ at 0.006%) was applied to a piece of filter paper and placed in a first section while an organic solvent (e.g., deionized water), was applied to another piece of filter paper and placed in second section. Flies were then released into the center control section and lids were placed on the Petri dishes. Within one hour observations indicated that the flies avoided the section treated with the exemplary compound, methyl anthranilate, and preferred to reside in the solvent section.

More specifically, 100 captive flies were used and the sections were approximately equal in size, e.g., 33% of total space per section. Flies were released into the neutral zone of each Petri dish and monitored after 15 minutes and one hour. The results indicate that the flies avoided the treated areas at concentrations of approximately 0.25% and approximately 0.025%, while the response of the flies to the treated areas was somewhat neutral at concentrations of approximately 0.0025% and relatively neutral at approximately 0.00025%. The results demonstrate that the exemplary compound methyl anthranilate has stimulating properties which cause insects to move from one area to another.

Trapping (e.g., Stick Trap Analog)

Trials were performed using an exemplary compound as part of a trapping device (e.g., a glue coated cardboard surface). Five traps were each treated with a 1 ml solution of 0.0156%, 0.03125%, 0.0625%, 0.125% and 0.25% methyl anthranilate, respectively. The treated traps were then placed at relatively random locations in a field. An untreated trap was placed adjacent to each treated trap and the number of insects adhered to each trap recorded as a function of time. Table 1 lists the results of this trial.

TABLE 1

Exemplary compound, methyl anthranilate.

| | 1 min | 5 min | 10 min | 20 min |
|---|---|---|---|---|
| Percent Concentration | | | | |
| 0.0156 | 3 | 22 | 75 | >75 |
| 0.0313 | 5 | 15 | 68 | >68 |
| 0.0625 | 7 | 35 | 128 | >128 |
| 0.1250 | 15 | 62 | 256 | >256 |
| 0.2500 | 43 | 84 | 346 | >346 |
| Untreated Trap No. | | | | |
| 1 | 0 | 0 | 0 | 0 |
| 2 | 0 | 0 | 0 | 0 |
| 3 | 0 | 1 | 1 | 1 |
| 4 | 0 | 0 | 0 | 0 |
| 5 | 0 | 0 | 0 | 0 |

An exemplary compound, methyl anthranilate (e.g. Bird Shield™) was applied at 0.025% concentration to a three foot by one foot (three square feet) section of aluminum siding (treated section) and compared with a equal sized section of aluminum siding (untreated section) on the side of a building.

Approximately 23 to 25 house flies (*D. melanogater*) had landed and were resting on each section. Immediately after the application of the exemplary compound to the treated section all of the flies departed. All of the flies on the untreated section remained. Thirty minutes after the application of the exemplary compound, approximately 30 flies attempted to land on the treated section within a five minute period of time but did not remain more than 6 to 8 seconds before leaving the area. Twenty-three flies remained on the adjacent untreated section. One hour after the application of the exemplary compound no flies were observed trying to land on the treated section while 15 flies remained on the untreated section. Twenty-four hours after the application of the exemplary compound no flies were observed on the treated section while 24 flies were recorded for the untreated section.

Applying Exemplary Compound after Applying Insecticide—Corn

An exemplary compound, methyl anthranilate, was applied to sweet corn after the crop had been treated with an insecticide (e.g., the pyrethrin insecticide WARRIOR™) to control corn ear worm (*Heliothus zea*). Prior to application of the exemplary compound, few if any larvae, which typically reside in the developing ear, were observed on the ground around the corn stalks.

After applying the exemplary compound, methyl anthranilate, at a concentration of approximately 4.5 oz. (127 g) per acre by aircraft, a significant number of insects were observed on the ground around the corn stalks. At harvest, approximately 2% of the corn plants treated with the insecticide alone (e.g., WARRIOR™) were observed to contain ear worms while observations of the corn plants treated with the insecticide (e.g., WARRIOR™) and the exemplary compound, methyl anthranilate, indicated that they did not contain any significant number of worms in the corn ears.

Applying an Exemplary Composition—Corn

An exemplary composition included an insecticide (e.g., the pyrethrin insecticide WARRIOR™) and an exemplary compound, methyl anthranilate. An exemplary method included applying the exemplary composition at a rate of approximately 4.5 oz. (127 g) of the exemplary compound per acre to sweet corn. Twenty-four hours after the application of the exemplary composition, the ground around the corn stalks was found to be littered with dead corn ear worm larvae. No corn ear worm larvae were found in the ears of corn treated with the exemplary composition. Corn that had not been treated with the exemplary composition contained one to five corn ear worm larvae per ear of corn, even after treatment with the insecticide (e.g., the pyrethrin insecticide WARRIOR™) alone.

Applying an Exemplary Composition—Sunflowers

An exemplary composition included an insecticide (e.g., the pyrethrin insecticide WARRIOR™) and an exemplary compound, methyl anthranilate. An exemplary method included applying the exemplary composition at a rate of approximately 4.5 oz. (127 g) of the exemplary compound per acre to sunflowers in an effort to control banded sunflower moth (*Cochylis hospes*).

Twenty-four hours after the application of the exemplary composition, the ground around the treated sunflowers was found to be littered with dead sunflower moth larvae. No banded sunflower moth larvae were found in the flowers treated with the exemplary composition, even seven days post-treatment. Sunflowers that had not been treated with the exemplary composition contained a significant number of (e.g., numerous) banded sunflower moth larvae, even after treatment with the insecticide (e.g., the pyrethrin insecticide WARRIOR™) alone.

Exemplary Comparison to DEET—Sunflowers

An exemplary compound, methyl anthranilate, was combined with long chain fatty acids and, in a trial, effectiveness of the mixture was compared to that of N,N-Diethyl-m-toluamide (DEET, which has a formula weight of approximately 191 and a water solubility of approximately 912 mg/L at 25° C.). DEET is often used by entomologists in standard procedures to draw sunflower seed weevils (*Smicronyx* spp.) out of the heads of sunflowers. In this trial, DEET was provided in the commercially available product DEEP WOODS OFF™ repellent (S.C. Johnson and Son's, Racine, Wis.), which has approximately 28.5% active ingredient; 1.5% other isomers and 70% inert ingredients. Forty-two flowers were randomly selected from interiors of three fields. One-half of the flowers were sprayed with the DEET containing repellent while the remaining flowers were sprayed with the exemplary compound at a concentration of approximately 0.00312% methyl anthranilate, which was combined with long chained fatty acids. The number of sunflower weevils was recorded. The results are presented in Table 2 and indicate that the exemplary compound, methyl anthranilate, was generally more effective than DEET, given the aforementioned conditions.

TABLE 2

Comparison to DEET product.

|  | DEET Number of insects | Methyl Anthranilate Number of insects |
|---|---|---|
| Field No. 1 Flower No. | | |
| 1 | 5 | 8 |
| 2 | 8 | 6 |
| 3 | 6 | 0 |
| 4 | 4 | 1 |
| 5 | 3 | 2 |
| 6 | 0 | 6 |
| 7 | 1 | 5 |
| 8 | 6 | 17 |
| 9 | 5 | 16 |
| 10 | 3 | 7 |
|  | Total 44; Mean = 4.4 | Total = 68; Mean 6.8 |
| Field No. 2 Flower No. | | |
| 1 | 7 | 23 |
| 2 | 18 | 24 |
| 3 | 12 | 26 |
|  | Total = 37; Mean = 12 | Total = 72; Mean = 24 |
| Field No. 3 Flower No. | | |
| 1 | 19 | 11 |
| 2 | 11 | 14 |
| 3 | 6 | 10 |
| 4 | 7 | 8 |
| 5 | 4 | 4 |
| 6 | 16 | 9 |
| 7 | 9 | 7 |
| 8 | 14 | 4 |
|  | Total = 86; Mean = 10.3 | Total = 67; Mean = 8.4 |

Applying an Exemplary Compound—Sunflowers

An exemplary compound, methyl anthranilate, was combined with long chain fatty acids. An exemplary method applied the mixture to fifteen maturing sunflowers in the interior of two fields that were previously sprayed with an insecticide, esfenvalerate (e.g., the insecticide product ASANA™). The mixture that included the exemplary compound was applied by spraying the mixture across the head of each flower (e.g., where seeds exist). The number of striped sunflower head moth larvae and weevils, emerging from the seeds, was recorded. The results presented in Table 3 indicate that the exemplary compound as included in the mixture was not only successful in drawing striped sunflower head math larvae out of the seeds but adult weevils as well after the crop had been treated with the insecticide alone.

TABLE 3

Exemplary Compound and Sunflowers

| Field No. 1 Flower No. | Number of Moth Larvae | Adult Weevils | Field No 2 Flower No. | Number of Moth Larvae | Adult Weevils |
|---|---|---|---|---|---|
| 1 | 1 | 2 | 1 | 0 | 1 |
| 2 | 0 | 0 | 2 | 0 | 6 |
| 3 | 1 | 0 | 3 | 1 | 1 |
| 4 | 1 | 0 | 4 | 1 | 0 |
| 5 | 0 | 1 | 5 | 3 | 0 |
| 6 | 0 | 0 | 6 | 0 | 0 |
| 7 | 1 | 0 | 7 | 1 | 0 |
| Total | 4 | 3 | | 6 | 8 |
| Mean | 0.57 | 0.43 | | 0.86 | 1.14 |

Applying Exemplary Compound after Exemplary Composition

An exemplary compound, methyl anthranilate, was combined with long chain fatty acids. The exemplary compound, as mixed with the fatty acids, was applied to three fields of maturing sunflowers. Each of the fields had previously been treated with an exemplary composition that included an exemplary compound, methyl anthranilate (approx. 4.5 oz per acre mixed with long chain fatty acids) and an insecticide, in this example, esfenvalerate (approx. 8 oz per acre using the insecticide product ASANA™). Ten flowers were randomly selected from the interior of each field and one-half of the seed heads were sprayed with DEET and one-half sprayed with the exemplary compound at a concentration of approximately 0.00312% methyl anthranilate, which was in a mixture that included long chain fatty acids. Spraying sprayed across the head of each flower. The number of striped sunflower head moth larvae, emerging from the seeds, was recorded. The results presented in Table 4 indicate a high level of effectiveness of the exemplary compound when applied after an exemplary composition.

TABLE 4

Exemplary Compound and Insecticide

| Flower No. | Field No. 1 Number of Larvae | Field No. 2 Number of Larvae | Field No. 3 Number of Larvae |
|---|---|---|---|
| 1 | 0 | 0 | 0 |
| 2 | 0 | 0 | 0 |
| 3 | 0 | 0 | 0 |
| 4 | 0 | 0 | 0 |
| 5 | 0 | 0 | 0 |
| 6 | 0 | 0 | 0 |
| 7 | 0 | 0 | 0 |

Exemplary Compound—Mosquitoes

An exemplary compound, methyl anthranilate was compared in trials to determine effectiveness of the exemplary compound relative to effectiveness of N,N-Diethyl-m-toluamide (DEET, which has a formula weight of approximately 191 and a water solubility of approximately 912 mg/L at 25° C.). In these trials, DEET was provided in the commercially available product DEEP WOODS OFF™ repellent (S.C. Johnson & Son, Inc., Racine, Wis.), which has approximately 28.5% active ingredient; 1.5% other isomers and 70% inert ingredients.

In a first trial, a human subject was exposed to a mosquito (*Aedes aegyptis*) rich environment without application of the exemplary compound or DEET. Within less than one minute the subject was covered with the insects. In a second trial, the subject sprayed one unclothed arm with the exemplary compound at a rate of 0.00312% and the other unclothed arm with DEET at a concentration of 0.24%. The subject's head remained untreated. Upon returning to the test area, the subject's head was covered with the insects within one minute. No mosquitoes were found on either arm of the subject treated with either methyl anthranilate or DEET. In a third trial the subject, after removing the DEET from his/her body, reapplied the exemplary compound to unclothed arms, head and neck before returning to the test area. The subject returned to and remained in the test area for more than one hour without any of the insects landing on his/her arms, hands and head while numerous insects were observed on the clothed portions of his/her anatomy. This particular example, demonstrated that the exemplary compound methyl anthranilate was as effective as DEET and at a lower concentrations when it was used as a mosquito repellent.

Exemplary Treatment of Insect Nests

As already mentioned, various aforementioned exemplary compounds that include a nitrogen atom have been shown to affect insect behavior. For example, methyl anthranilate and methyl nicotinate are insect semiochemicals released from the postpygidial gland of worker African army ants (e.g., Aenictinae *Aenictus* sp. nova, other *Aenictus*, etc.) and o-aminoacetophenone is an insect semiochemical released from queen honey bees (e.g., *Apis mellifera* L., other *Apis*, etc.) and apparently not from worker bees.

An exemplary method includes applying an exemplary compound or an exemplary composition to an insect nest. For example, a trial applied methyl anthranilate, in a diluted form, to an ant nest and upon observation at about 24 hours post-application, no ant activity was observed at the site of the nest.

An exemplary method includes dispersing insects from a nest by applying an insect semiochemical to the nest or proximate to the nest. For example, such semiochemicals may be "trail" chemicals. Once the ground or nest region is "polluted" by such chemicals, deposition of such chemicals by insects no longer serves to clearly mark a trail.

Exemplary Treatment of Ground

An exemplary method includes applying an exemplary compound or composition to the ground to thereby discourage insect traffic or deposition of insect semiochemicals. For example, where an exemplary compound is applied to the ground, the ground is not readily further marked by an insect semiochemical. A trial was performed where an exemplary compound (methyl anthranilate) was applied to the ground to form a boundary. Upon observation, ants did not cross this boundary.

Exemplary Treatment of Large Storage Structures

An exemplary method includes positioning a container in a large storage structure (e.g., storage building, a barn, a hanger, a silo, etc.) wherein the container contains an exemplary compound (e.g., methyl anthranilate). In this example, release of the compound occurs over time.

A trial was performed where a 2.5 gallon HDPE container at least partially filled with methyl anthranilate was positioned in an aircraft hanger that also had a population of birds that would leaving guano (e.g., on aircraft). After placement of the container containing the compound in the hanger, bird population dwindled and the aircraft experienced a significant drop in surface guano.

Exemplary Time Release Devices

While the HDPE container has already been mentioned, other exemplary time release devices include porous bodies or other bodies that can contain an exemplary compound and release the exemplary compound over time.

An exemplary device is a tube with a permeable wall. The tube is filled with an exemplary compound such as, but not limited to, methyl anthranilate. The tube is then used to form a boundary. For example, a garden prone to ants may be protected by placing the exemplary time release device around the garden. The device may be surface positioned or buried. The effect of the time release device is to deter insects and/or birds.

An exemplary container includes a formulation that comprises methyl anthranilate, fatty acid and monoethanol amine or triethanolamine wherein the container allows for time release of the formulation over a period of one month or more. Other containers and formulations are possible as well.

Exemplary Formulations Including One or More Amines

Exemplary formulations include an exemplary compound and one or more other components. An exemplary formulation may be an emulsion, for example, a multiphase mixture. Molecules that act as surface active agents, i.e., surfactants, are useful in forming emulsions. An exemplary formulation may be or include an exemplary composition.

In one example, an emulsion is provided as a bird repellant. In this example, the emulsion includes an exemplary compound that repels birds (e.g., methyl anthranilate). Upon application, the emulsion is configured to deter birds from various agricultural crops such as seed crops and edibles, including berries, corn, grapes, newly planted seeds, ripening grain crops, etc. The odor and/or taste of the emulsion may cause the birds to avoid such crops; other applications are possible where deterrence of birds is desired. For example, the emulsion may be applied to harvested and/or stored crops, such as corn or grain, to other birds, to physical spaces including bird-nesting areas, barns, animal boarding facilities, grassy areas such as parks, sports fields, etc. In various other instances, the emulsion is provided to affect insects and optionally repel birds.

In one specific example described in detail herein, amine functional agents may be mixed with any suitable repellant compound. For example, consider the aforementioned amine agents monoethanolamine, diethanolamine, and triethanolamine. An exemplary formulation may optionally use a combination of an amine agent and a metal agent (e.g., NaOH, KOH, etc.).

Exemplary repellants include compounds using the active ingredient in U.S. Pat. No. 2,967,128 to Kare, as well as other suitable bird repellant compounds, including, but not limited to, benzoic derivatives of esters of anthranilic acids, esters of phenylacetic acid, or dimethyl benzyl carbonyl acetate. Exemplary repellants for use in the emulsion disclosed herein include the following compounds and combinations of these compounds: methyl anthranilate, dimethyl anthranilate, ortho-amino acetophenonone, 2-amino-1,5-dimethyl acetophenone, veratroyl amine, cinnamic aldehyde or esters.

The repellants, such as methyl anthranilate, when applied directly to plants exhibits various levels of phytotoxicity (plant toxicity). Moreover, various repellants may be light sensitive such that exposure to light may result in loss of primary odor and taste repellant properties.

The use of an emulsification agent with the repellent enables emulsification of the repellant, such as methyl anthranilate, in an aqueous medium. Of course, phases may have various hydrophilic/hydrophobic characteristics (e.g., oil-in-oil, oil-in-water, water-in-oil, etc). The repellant may be contained within micelles or globules formed around the repellant by the emulsification agent.

An exemplary formulation optionally includes liquid crystal structures. For example, multilamellar bodies can be formed using surfactants where phases of a mixture are stabilized. Cross-polar microscopy and other techniques are useful for examining such bodies. Specialized polymers can also help to stabilize liquid crystalline structures.

The emulsification of the repellant may prevent the direct contact of the repellant with the physical surface of the crops, and therefore, reduces the phytotoxic effects of the repellant. Although the repellant may be contained in a micelle within an emulsion, the potentness of the repellant, as a bird repellant, is substantially retained. Further, depending on specifics of formulation, time release may be achieved through judicious choice of formulation components.

As described in more detail below, an exemplary method and composition is provided which includes providing a repellant and an amine emulsifying agent. The method further includes adding the amine emulsifying agent to the repellant to generate a stable, ready-to-apply emulsification. It should be appreciated that in some embodiments, the amine emulsifying agent may be provided alone or in combination with other types of emulsifying agents, such as alkali metal salts. Moreover, an amine emulsifying agent may be added to preformulated repellants or previously mixed emulsions; to improve the stability of the prior products.

Various amine functional agent (also referred to herein as an amine emulsifying agent) may be used. For example, mono, di- and tri-substituted alkanolamines and mono, di and tri substituted alkyl amines may be used. Additionally, cyclic aliphatic and aromatic amines, including mono and multi-substituted cyclic amine compounds may be used. For example, heterocyclic amines with ring or side chain amine functionality may be used.

Two specific amine agents are triethanloamine and methyl anthranilate, however other suitable amine functional agents are considered and may be used without departing from the scope of the disclosure: It should be noted that methyl anthranilate, in addition to be a repellant, may also be useful as an amine agent for making the amine emulsifying agent (e.g. the salt) described above.

In other words, the emulsion may be understood to be a mixture of a repellant and an anionic salt of an amine or mixtures of amines (and optionally one or more alkali metal) and a fatty acid or mixtures of fatty acids. While fatty acids are mentioned, anionic surfactants may be used. For example, an acid form of an anionic surfactant may be neutralized with an amine or other agent to form a salt.

The amine may react with the fatty acid in an appropriate stoichiometric ratio to form a soap-like material. This soap-like material is a suitable emulsification agent for the product described herein. Typically, the fatty acid may be a 010 to 018 fatty acid, however it is possible to use fatty acids with longer and/or shorter carbon chains. The fatty acid may be a saturated or unsaturated fatty acid and the carbon atoms in the fatty acid may be linear, cyclic, and/or branched carbon chains, or combinations thereof.

An exemplary product is 2-aminobenzoic acid methyl ester (methyl anthranilate). When the product is added to an amine-based soap, an emulsion is formed with an evenly distributed composition having little or no propensity for separation either in the concentrated or diluted form. Other suitable mixtures of a repellant and an amine emulsification agent may be used without departing from the scope of the disclosure.

The composition of the emulsion may be provided in a wide range of weight or volume ratios. Further, the amount of emulsifying agent may depend on the type of application. Similarly, the level of dilution of the product may depend on the application. For example, the amount of emulsifying agent may be balanced based on the individual plant phytotoxic levels and the application time period relative to harvest or exposure to birds.

As an example and not as a limitation, an emulsion may be provided with 1:500 to 1:1 repellant to fatty acid salt ratio.

As briefly mentioned above, typically the composition (repellant and emulsifying agent) may be diluted using an aqueous solution, such as water or other carrier or dispersal agent. Dilution may occur by farm workers immediately prior to application. Alternatively, since the product remains stable, the product may be diluted substantially earlier than an intended application. Moreover, the product may be stored in the diluted state for use in the future. Depending on the application, once diluted to a select amount, the product may be applied to the desired crops, surface, etc. Any suitable dispenser may be used to apply the product. For example, portable sprayers, sprinklers, crop dusters, etc. may be used to apply the product.

While the foregoing mentions a repellant as an exemplary compound in a formulation, again, an exemplary compound may act to affect insect behavior.

The amino agent, which when formed into a fatty acid soap by association of the amine function with the fatty acid, provides a stable emulsion which does not separate significantly on standing or storage. Such a formulation provides more stability then prior emulsions whereby alkali metal salts are used in similar formulations with fatty acids. For example, the formulation is an improvement to the emulsion disclosed in U.S. Pat. No. 5,296,226 to Askham and incorporated by reference above. It should be appreciated that, unlike prior formulations, the disclosed emulsion due to use of the amine functional group, is stable in both a pre-diluted form and a diluted form and does not easily separate out. For example, the emulsion typically is stable over a wide range of temperatures and temperature fluctuations and for extended period of times.

Where time release of an exemplary compound is to occur, stability of the compound in the formulation is generally desired. Thus, an exemplary formulation may be stable for an extended period of time without the exemplary compound and stable for an extended period of time (e.g., months) with the exemplary compound. Thus, as the exemplary compound leaves the formulation (e.g., via evaporation), the formulation remains stable. In other words, in this example, the formulation does not become unstable due to a change in concentration of the exemplary compound (e.g., methyl anthranilate).

Figure 2:
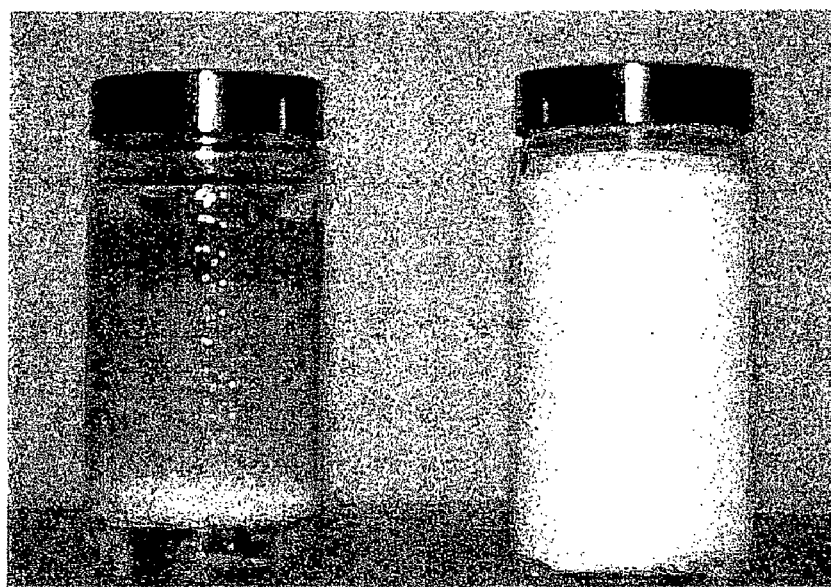
FIG. 2 is a photograph comparing a bird repellant with an emulsion using an alkali metal salt with an emulsion using an amine-based functional group.

FIGS. 1-4 further illustrate the stability characteristics of the disclosed amine emulsion. Specifically, FIG. 1 is a photograph comparing a bird repellant product with an emulsion using an alkali metal salt with an emulsion using an amine-based functional group. Both products were made approximately one-month prior to the photograph. As shown, the alkali metal salt emulsion has significant separation, while the amine-based emulsion remains stable and substantially unseparated. Similarly, FIG. 2 is a photograph showing the separation of a conventional bird repellant with an emulsion using an alkali metal salt after over a year of storage.

Figure 3:
FIG. 3 is a photograph comparing a triethanolamine emulsion and a methyl anthranilate emulsion added to a standard bird repellant emulsion.
Figure 4:
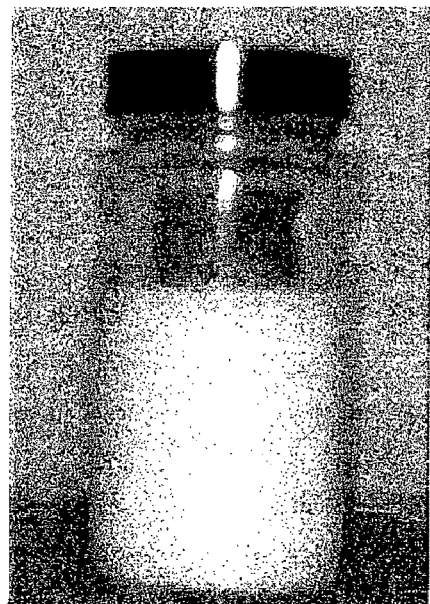
FIG. 4 is a photograph showing a triethanolamine emulsion diluted to application strength.

FIG. 3 further is provided to show a triethanolamine emulsion after a year of storage. FIG. 3 further shows a methyl anthranilate emulsion added to a standard alkali metal bird repellant emulsion after over, a year of storage. FIG. 4 is a photograph showing a triethanolamine emulsion diluted to a particular application strength. It should be noted that the product has not separated and retains its emulsified state upon dilution.

Long-term storage of the emulsion is possible due to the stability of the emulsion. Since the emulsion is able to retain its emulsified state, the product may remain mixed and ready to use as it sits on a shelf. Unlike prior bird repellants, including compositions using alkali metal salts, which upon a short period separated out, the present emulsion retains the emulsified state and does not require mixing to attempt to recombine the product. In instances of extreme conditions where some separation does occur, re-emulsification may occur with a minimal amount of energy input (e.g., heating, shaking, re-stirring, etc.).

During storage, temperatures at or below 40 degrees Fahrenheit may result in some precipitation of the product. The repellant, such as methyl anthranilate, typically will crystallize out at such temperatures. However, unlike alkali metal salt emulsions where separation of the emulsion prior to crystallization causes re-emulsification to be difficult, re-emulsification of amine anionic salt emulsions may occur more easily upon warming of the product.

Various exemplary formulations may be easier to apply and use in agricultural settings then prior bird repellant formulations. Specifically, an exemplary formulation, when formulated as an emulsion, typically retains its emulsified state without separation upon dilution to a concentration suitable for agricultural application. By remaining in the emulsified state, the emulsion may be ready to apply without significant mixing required. Thus, farm workers do not need to spend significant periods of time attempting to mix the product prior to application or during application. Moreover, machinery for application of the product is simplified due to the minimal mixing requirements of the product since the emulsified state of the product is substantially retained. In other words, the maintenance of the emulsified state during dilution enables ready-to-use product for application.

With respect to application via a spray system, surface tension and other properties are optionally adjusted for optimal spraying (e.g., spray angle, spray pressure, etc.). In general, as the surface tension decreases, the spray angle increases. Further, breakup and droplet size are typically affected by the surface tension of the formulation sprayed. Other concerns for longevity of spray equipment may also be taken into affect. For example, where foaming is an issue, an exemplary formulation may include an antifoam agent.

Various exemplary formulations optionally have a lower pH value than prior bird repellants. For example, in conventional emulsions made with alkali metal salts, the pH value of such solutions may be 9.6 (see, e.g., Askham). However, the emulsion made with anion salts of amines can be adjusted to have a lower pH, for example, of about 7.8. The lower pH may make use of the product safer. For example, the lower pH product may be less of an irritant to the skin and eyes then previous products.

Testing was done to confirm that an exemplary formulation, formulated as an amine emulsion, was as effective as other bird repellant products. Exemplary field tests include preliminary results finding the absence of phytotoxicty when the above product was applied to sunflowers at up to two times normal application rate. Moreover, field tests reported that application of the product to wild-rice and sweet corn had similar results as emulsions using alkali metal salts in regards to bird-repellency effects.

An exemplary formulation may further be used in other applications, including, but not limited to, use to affect insect behavior, use with insecticides, use as a flavor-dispersing agent, etc. For example, an exemplary emulsion may be used in the preparation of a mixture of insecticides. Many insects communicate with pheromones. Pheromones can include terpenoids, aliphatic aldehydes, ketones, esters, etc. Such pheromones may be sex attractants, alarm pheromones, aggregation pheromones, trail pheromones and the like. In addition, various bird repellant products have been approved by regulatory agencies for mixing with *bacillus thuringensis*, insecticides, fungicides and herbicides.

The presently disclosed amine functional emulsification agents may be used in the preparation of mixtures of insecticides and the alarm pheromone methyl anthranilate. It should be noted that methyl anthranilate in addition to being a bird repellant is also useful as an alarm pheromone for many classes of insects. Use of these emulsions as dispersing agents for pheromones, alone or in conjunction with repellants, may provide the same protection from separation, phytotoxicty and the benefits of a mild pH as described for the bird repellant function.

As another example, surface-active agents, including emulsifying agents, may be useful as flavor-dispersing and/or flavor-enhancing agents. For example, emulsifying agents, including potassium salts have been described as useful surface-active agents for flavor-dispersing agents in U.S. Pat. No. 4,284,654 to Trenkle et al., the disclosure of which is incorporated by reference for all purposes. Use of the presently disclosed amine emulsion may provide an improved flavor-dispersing agent as it provides a more stable composition that may be more readily applied, stored, and used then previous surface-active agents. Moreover, the lower pH of the emulsion may enhance or aid in introducing flavor to a target product, such as edibles and the like.

An exemplary formulation may include methyl anthranilate, fatty acid and an amine agent that can form a surfactant with the fatty acid (e.g., monoethanolamine, triethanolamine, etc.). Such an exemplary formulation optionally includes sulfite. The fatty acid optionally includes saturated fatty acid, predominantly saturated fatty acid or only saturated fatty acid (i.e., no unsaturated fatty acid). Such an exemplary formulation may be in the form of an emulsion. Such an exemplary formulation may include water and/or an antifoam agent. Such formulation optionally has a mass percentage of methyl anthranilate that exceeds approximately 10% of the total formulation mass. Such a formulation optionally has a pH is less than about 8.

An exemplary method of making a formulation includes providing ingredients water, fatty acid, one or more amine agents (e.g., monoethanolamine, triethanolamine, etc.), methyl anthranilate or other insect affecting compound or bird affecting compound and optionally one or more other ingredients. The exemplary method includes mixing the various ingredients, optionally in a manner whereby the fatty acid is not exposed to a pH that could cause degradation of the fatty acid to carbonyls, for example, not exposing the fatty acid to a pH greater than about 9. Of course, time/pH or other factors may be taken into account (e.g., temperature, etc.). The exemplary method optionally employs mixing in an environment with an oxygen concentration less than atmospheric. Other ingredients optionally include sulfite where the sulfite may inhibits Schiff base formation in the formulation (e.g., carbonyl amine reactions, especially where methyl anthranilate is involved).

The exemplary formulation made by this example method is optionally applied to an ant nest, other insect nest, the ground, etc. Such an exemplary formulation is optionally contained in a time release container that releases the methyl anthranilate over a period of months. Further, as the concentration of methyl anthranilate decreases, the formulation may remain stable. The formulation according to such an exemplary method is optionally an emulsion. The formulation according to such an exemplary method optionally has a mass percentage of methyl anthranilate that exceeds approximately 10% of the total mass of the formulation. The fatty acid of this exemplary method optionally includes saturated fatty acid.

Example Exemplary Formulation

An example formulation included water (300 ml), triethanolamine (TEA 15 g), E-610 fatty acid (FA 28 g), antifoam agent (AF 1 g), methyl anthranilate (MA 50 g, e.g., about 12.7%). The formulation was made in a blender where water was added. Upon stirring the triethanolamine was added followed by the antifoam agent. The fatty acid was added slowly (approx. average molecular weight 278). A clear solution resulted. Then the methyl anthranilate was added slowly and the mixture stirred for about 1 minute. At about 4 months the formulation was stable with a slight yellowing. At about 10 months, the formulation was stable.

Another example formulation included water (250 ml), TEA 10.7 g, FA 20 10 g, AF 1 g and MA 90 g. Yet another example formulation included water (250 ml), TEA 17.9 g, FA 33.4 g, AF 1 g, and MA 90 g (about 20%). This formulation was thick and viscous and 50 ml of water was added to thin. Another example formulation included water (250 ml), diethanolamine 12.6 g, FA 33.4 g, AF 1 g, and MA 47 g. More water was added before MA addition (70 ml). Another 15 example included water (6,000 ml), TEA 385 g, FA 668 g, and MA 1,800 g (about 20%). These examples exhibited emulsion stability and were tested as “acceptable” for phytotoxicity in a diluted form.

Additional Exemplary Formulations

An article by Leong and Bettens, “Modeling the Maillard Reaction: Schiff Base Formation”, Ann. N.Y. Acad. Sci. 1043: 890 (2005), discusses Schiff base formation whereby an amine and a carbonyl (e.g., aldehyde or ketone) react and to produce colored products. Sometimes this is referred to as nonenzymatic browning. Schiff base formation is pH dependent and is known to occur slowly under acid conditions. An exemplary formulation may avoid or reduce occurrence of Schiff base (or associated reactions) in various manners.

The exemplary compound methyl anthranilate is known to participate in Schiff base reactions. For example, see U.S. Pat. No. 4,853,369 entitled “Schiff base reaction product of ethyl vanillin and methyl anthranilate and organoleptic uses thereof”, which is incorporated by reference herein, and U.S. Pat. No. 4,840,801, entitled “Use of Schiff base reaction product of methyl anthranilate and canthoxal in augmenting or enhancing aroma or taste of foodstuff or chewing gum”, which is incorporated by reference herein. Thus, an exemplary formulation that includes methyl anthranilate or other exemplary compound optionally includes one or more components that act to minimize or reduce Schiff base reactions involving the exemplary compound. Yet further, minimization or reduction of such reactions may occur through preparation techniques (e.g., sequence of events, controlled atmosphere, cooling, heating, pH control, etc.).

U.S. Pat. No. 5,518,644, entitled “Aqueous built liquid detergents containing a sulfite salt to inhibit color alteration caused by mixture of alkanolamines and perfumes”, which is incorporated by reference herein, discloses use of sulfite or sulfiting agent in a laundry detergent that includes an alkanolamine component. An exemplary formulation optionally includes such a sulfite or sulfiting agent to preserve the formulation (e.g., color or other aspect).

An exemplary formulation includes a sulfite or sulfiting agent. Sulfiting agents (sulfur dioxide, sodium sulfite, sodium and potassium bisulfites and metabisulfites) have been added to many foods to prevent enzymatic and nonenzymatic browning; control growth of microorganisms; act as bleaching agents, antioxidants, or reducing agents; and carry out various other technical functions. Sulfites inhibit nonenzymatic browning by reacting with carbonyl intermediates, thereby preventing their further reaction to form brown pigments.

Fatty acids can degrade via various mechanisms. For example, fatty acids can degrade via oxidation as is common in spoilage of foodstuffs. Atmospheric oxygen or other sources of oxygen participate in autoxidation reactions that cause degradation of fatty acids. Cleavage products which have been identified after autoxidation of fatty acids include saturated straight chain carboxylic acids, dicarboxylic acids and a variety of alcohols, aldehydes and ketones (see, e.g., Mittet, "The Degradation of Tall Oil Fatty Acids by Molecular Oxygen in Alkaline Media", PhD Dissertation, The Institute of Paper Chemistry, Appleton, Wis., January 1979, which is incorporated by reference herein). Various products of fatty acid degradation can therefore participate in Schiff base reactions with an amine or amines. An exemplary method includes mixing an exemplary formulation in a reduced oxygen environment or in a manner that does not increase oxygen concentration in components due to atmospheric oxygen. Further, a container optionally prevents or limits oxygen transfer from the surroundings to the exemplary formulation contained in the container.

Other common initiators of fatty acid degradation are free radicals and ultraviolet light. Thus, a colored container, an opaque container, etc., may be used to diminish exposure of fatty acids in an exemplary formulation to UV radiation.

An exemplary formulation includes saturated fatty acids. Saturated fatty acids and their esters tend to be more resistant to reaction with oxygen-alkali compared to unsaturated fatty acids. While all fatty acids are subject to reaction with oxygen, saturated fatty acids tend to be autoxidized very slowly unless relatively severe conditions are imposed. Since saturated fatty acids do not contain carbon-carbon double bonds, the oxidations are not as specific as analogous reactions involving unsaturated compounds. Saturated fatty acids include, but are not limited to, $CH_3(CH_2)_{10}CO_2H$ (lauric acid, MP 45° C.), $CH_3(CH_2)_{12}CO_2H$ (myristic acid, MP 55° C.), $CH_3(CH_2)_{14}CO_2H$ (palmitic acid, MP 63° C.), $CH_3(CH_2)_{16}CO_2H$ (stearic acid, MP 69° C.), $CH_3(CH_2)_{18}CO_2H$ (arachidic acid, MP 76° C.). An exemplary formulation optionally uses saturated fatty acids, unsaturated fatty acids, or a mix of saturated and unsaturated fatty acids.

What is claimed is:

1. A method of making a stable formulation for affecting insects, birds or insects and birds, the method comprising:
    providing water;
    providing fatty acid;
    providing triethanolamine to achieve a mass percentage of triethanolamine that exceeds approximately 2.8% of the total mass of the formulation;
    providing methyl anthranilate sufficient to achieve a mass percentage of methyl anthranilate that exceeds approximately 10% of the total mass of the formulation; and
    mixing portions of the water, the fatty acid, the triethanolamine and the methyl anthranilate in a manner whereby the fatty acid is not exposed to a mixture pH greater than about 9 and whereby at least some of the fatty acid and at least some of the triethanolamine form a surfactant to enhance formulation stability as a concentrated formulation and as a diluted formulation.

2. The method of claim 1 wherein the mixing occurs in an environment with an oxygen concentration less than atmospheric.

3. The method of claim 1 further comprising providing sulfite.

4. The method of claim 3 wherein the providing sulfite inhibits Schiff base formation in the formulation.

5. The method of claim 1 further comprising applying the formulation to an ant nest.

6. The method of claim 1 further comprising containing the formulation in a time release container that releases the methyl anthranilate over a period of months.

7. The method of claim 6 wherein as the concentration of methyl anthranilate decreases, the formulation remains stable.

8. The method of claim 1 wherein the formulation comprises an emulsion.

9. The method of claim 1 wherein the fatty acid comprises saturated fatty acid.

10. The method of claim 1 further comprising providing at least one alkali metal salt that comprises a metal selected from a group consisting of sodium and potassium and adding the at least one alkali metal salt to the formulation.

11. The method of claim 1 further comprising diluting the formulation to provide a diluted formulation.

12. The method of claim 11 wherein the diluted formulation comprises acceptable phytotoxicity for applying to a crop.

13. The method of claim 11 wherein the diluted formulation comprises micelles.

14. The method of claim 1 wherein the formulation comprises an emulsion and further comprising storing the formulation at a temperature at or below 40 degrees Fahrenheit.

15. The method of claim 14 further comprising re-emulsifying the formulation wherein the re-emulsifying comprises heating the formulation.

* * * * *